United States Patent [19]

Georgi et al.

[11] Patent Number: 4,850,305
[45] Date of Patent: Jul. 25, 1989

[54] ARTIFICIAL SYSTEM AND METHOD FOR BREEDING FLEAS

[75] Inventors: Jay R. Georgi, Freeville; Susan E. Wade, Ithaca, both of N.Y.

[73] Assignee: Cornell Research Foundation, Inc., Ithaca, N.Y.

[21] Appl. No.: 127,412

[22] Filed: Dec. 2, 1987

[51] Int. Cl.⁴ .............................................. A01K 45/00
[52] U.S. Cl. .......................................... 119/1; 119/30; 119/51 R; 422/102
[58] Field of Search .................... 435/287, 290; 119/1, 119/30, 31, 15, 51 R, 35; 422/99, 102

[56] References Cited

PUBLICATIONS

Bar-Zeev, M., et al, Entomol. Exp. & Appl. 5:60–68, 1962.
Bernardo, M. J., et al, J. Med. Ent., 23, No. 6, 666–679, 12/86.
Cerwonka, R. H., et al, J. Parasitology, 44, No. 5, 565–566, 1958.
Galun, R., Life Sciences, 5:1335–1342, 1966.
Kartman, L., Experimental Parasitology, 525–537 (1954).
Lauer, D. M., et al, J. Med. Ent., 14, No. 5, 595–596, 2/78.
Popular Mechanics, 11/87, p. 68.
Popular Science, 1/88, p. 8.
Rutledge, L. C., et al, Mosquito News, pp. 407–419, 12/64.
Sgovina, K. Parasitenk, 7:539–571 (1935).
Totze, R., Zentralbl. Bakt. Parasitenk. Infekt. 132, : 382–384 (1934).
Veterinary Viewpoints, No. 1, 1987, 4/87.

Primary Examiner—Barry S. Richman
Assistant Examiner—T. J. Wallen

[57] ABSTRACT

A system for breeding fleas comprises a blood reservoir with a feeding membrane and a feeding and reproduction chamber which either has a height dimension of 1.4 to 1.8 mm so as to restrict jumping by the fleas or includes fibrous material so the fleas can walk thereon substantially to a feeding location thereby reducing the amount of jumping required by the fleas to reach the feed location. The method involves providing access by the fleas to a blood food supply for at least 18 continuous hours and influencing the fleas to conserve energy expenditure either by restricting jumping by the fleas or by providing a walking path permitting the fleas to walk substantially to the feed location so as to reduce the amount of jumping required to feed. The feeding period and the system whereby the fleas conserve energy expenditure because they are either restricted from jumping or given an alternative to jumping enables obtaining practical reproduction outputs, i.e., at least 10% of the reproduction output of fleas feeding on host animals.

19 Claims, 3 Drawing Sheets

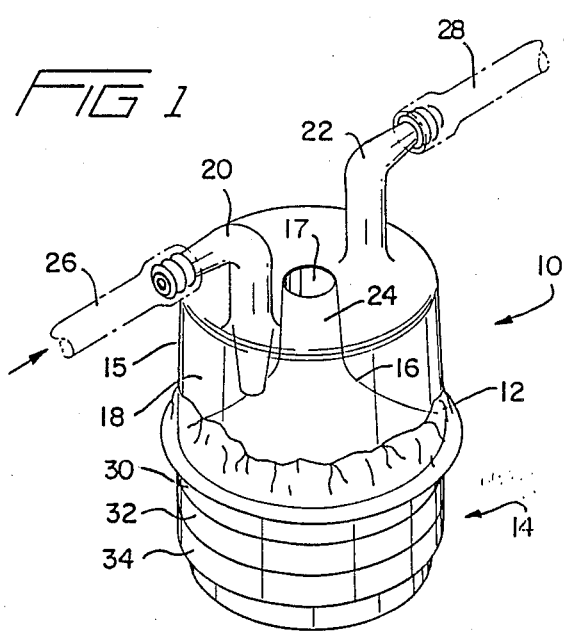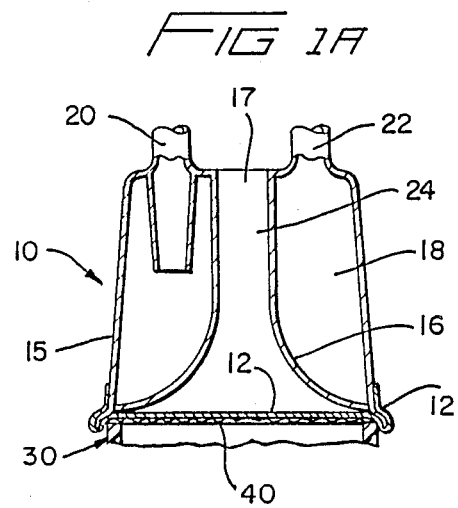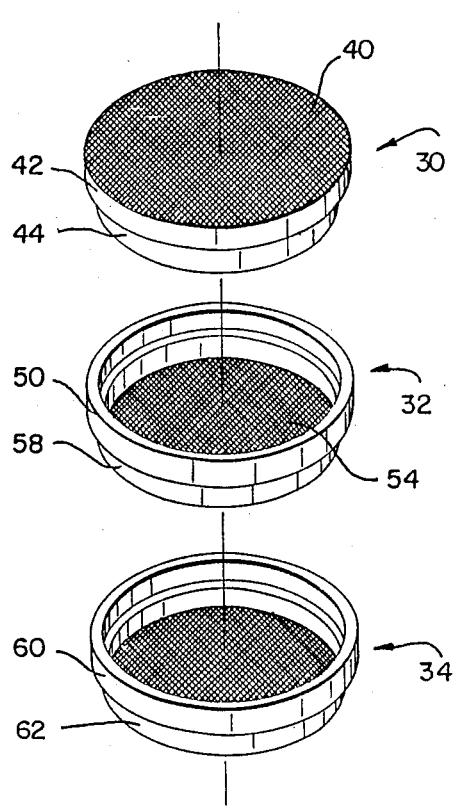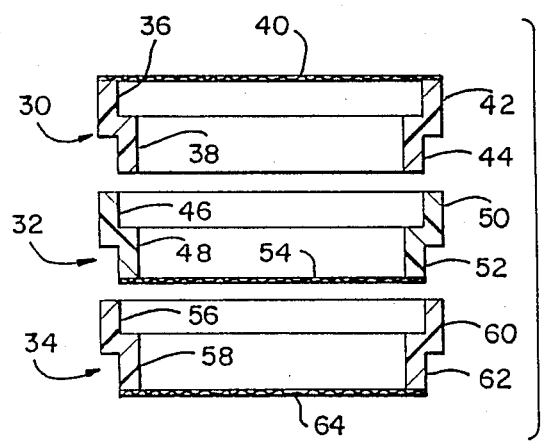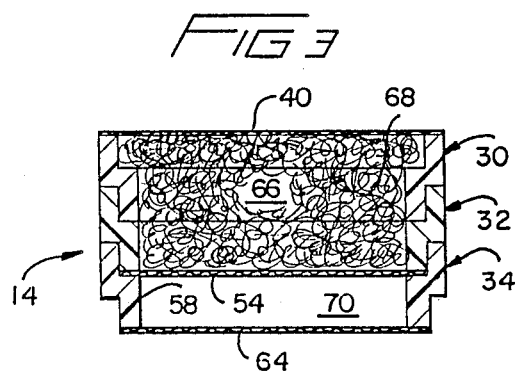

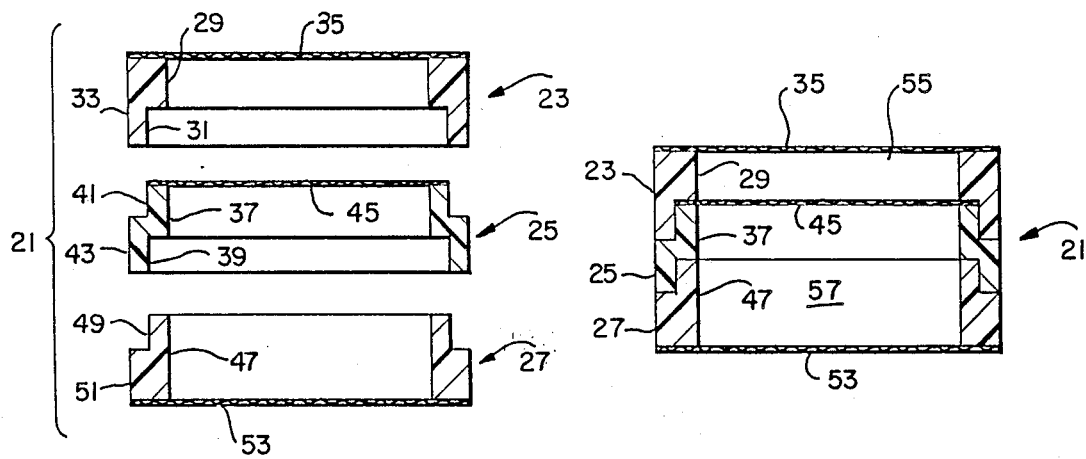
FIG 9
FIG 10
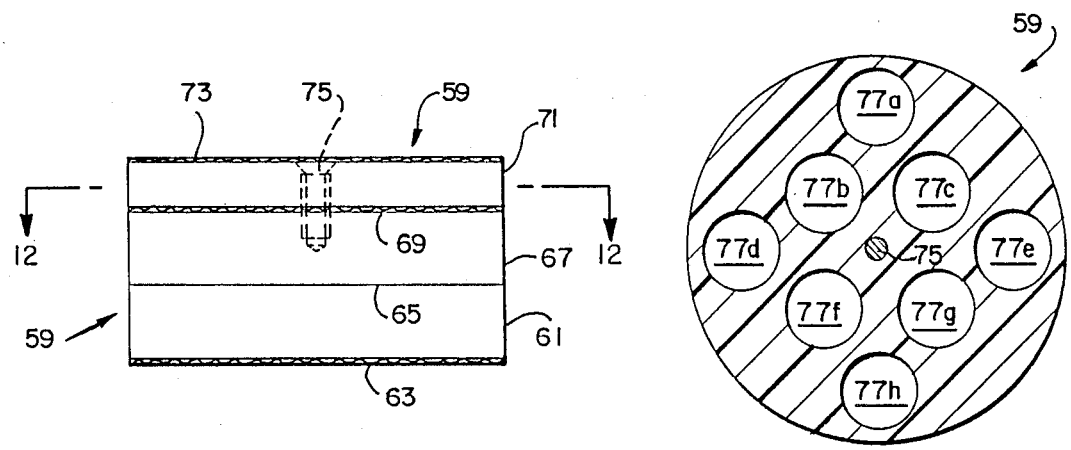
FIG 11
FIG 12

ARTIFICIAL SYSTEM AND METHOD FOR BREEDING FLEAS

TECHNICAL FIELD

This invention is directed to the in vitro breeding of fleas, i.e. the breeding of fleas in artificial systems where they do not feed on animal hosts. The fleas producted by the system and method herein are useful for research purposes e.g. to test the effect of growth regulators or toxicants, to study the transmission of blood borne disease organisms and parasites to fleas, to determine causes of allergies in animals bitten by fleas, to develop antiflea vaccines, to isolate and maintain strains of fleas possessing distinctive biological traits such as drug resistance or allergenicity. The invention reduces the need for animal hosts thereby decreasing the cost of research and public relations problems associated with using animals in research. The invention also allows more exact control of conditions compared to breeding programs relying on feeding on live hosts.

BACKGROUND OF THE INVENTION

In vitro feeding of hematophagous insects, including fleas, using systems comprising a cage, a food supply in a container with a feeding membrane and a food supply temperature control system have long been known. Such a system may comprise a Rutledge-type membrane feed (described in Rutledge, L.C., et al *Mosquito News*, pp. 407-419, December, 1964) with host blood therein as food with water circulating therethrough to control the food (blood) temperature. Successful feeding of fleas has been reported by Bar-Zeev and Sternberg, Entomol. Exp. & Appl. 5:60-68, 1962; Cerwonka & Castillo, J. Parasitol. 44:565-566, 1958; Galun, Life Sci 5:1355-1342, 1966; Kartman, Expr. Parasitol. 3:525-537, 1954; Lauer & Sonenshine, J. Med. Entomol. 14:595-596, 1978; Totze, Zentrabl. Bakt. Parasitenk. Infekt. 132:382-384, 1934. Only Lauer and Soneshine mention observing mating, ovipositing and viable larval production, but they do not report reproduction outputs. Lauer and Sonenshine reort feeding times of 1-5 hours in a feeding chamber which is a 2 cm diameter by 5 cm high black plastic cylinder installed directly above a feeding membrane; these conditions do not enable practical flea breeding.

One object of this inventio is to provide a system and method for practical breeding of fleas, utilizing an artificial system and method, i.e. a system and method which does not rely on feeding on a host animal. The term "practical breeding" of fleas is used herein to mean breeding to obtain a reproduction output at least 10% of the reproduction output of fleas feeding on host animals. While breeding of mosquitoes and flies has been obtained based on artificial systems, the breeding of fleas relying on such systems is much more difficult. Prior to the invention herein, the inventors of the present application know of only one report of breeding fleas relying on an artificial system, and that is in the Lauer and Sonenshine article described above where the conditions utilized do not provide practical breeding. Thus, the invention herein is a unique accomplishment.

SUMMARY OF THE INVENTION

It has been discovered herein that the above object is obtained by modifying the conventional feeding system and method described above by providing access by the fleas to a blood food supply for at least 18 continuous hours and providing means influencing the fleas to conserve energy expenditure either by restricting jumping by the fleas or by providing a walking path permitting the fleas to walk substantially to the feed location so as to reduce the amount of jumping required to feed.

The system herein for breeding fleas without providing access of the fleas to host animals comprises (a) blood reservoir means having a feeding end comprising blood supporting means penetrable by flea mouth parts for feeding and which preferably is self sealing to a substantial degree after feeding.

(b) means to maintain blood in said reservoir means at a selected temperature level, (c) feeding and reproduction chamber means to house fleas for breeding, said chamber means having a feeding end and an egg discharge end, the feeding end of said chamber means being juxtaposed to the feeding end of the blood reservoir means and comprising reticulated means having interstices sized to allow passage of flea mouth parts therethrough for feeding but to prevent escape of fleas therethrough, (d) means influencing approach of said fleas to said feedng end to conserve energy expenditure by said fleas.

In one preferred embodiment of the system herein, the means (d) comprises providing the interior of the chamber means (c) with a height dimension so as to restrict jumping of fleas in said chamber means (c). A height dimension ranging from 1.4 to 1.8 mm is considered suitable for this purpose.

In a second preferred embodiment of the system herein, the means (d) comprises fibrous material in said chamber means (c) permitting fleas to walk thereon substantially to said feeding end of said chamber means (c).

The method herein for breeding fleas without providing access of the fleas to host animals comprises (a) confining fleas in a breeding zone having a feeding end and an egg discharge end, (b) providing an inanimate flea-accessible source of host animal blood at a selected temperature at said feeding end, (c) maintaining the fleas in said breeding zone with access to said blood for a period of at least 18 continuous hours while influencing the approach of said fleas to said feeding end to conserve expenditure of energy by said fleas, thereby to foster feeding, mating and egg production, (d) discharging eggs from said breeding zonen and recovering said egge fro production of adult fleas therefrom.

In the method herein said influencing of the approach of said fleas to said feeding end of the breeding zone in one preferred embodiment comprises restricting jumping by the fleas in the breedign zone and in another preferred embodiment comprises providing a walking path whereon the fleas can walk substantially to the feeding end of the breeding zone.

BRIEF DESCRIPTION OF THE DRAWINGS

While the specification concludes with claims particularly pointing out andn distinctly claiming the subject matter of the present invention, it is believed the invention will be better understood from the following description taken in connection with the accompanying drawings in which:

FIG. 1 is a perspective view of one embodiment of a system herein.

FIG. 1A is a partial sectional view of the embodiment of FIG. 1.

FIG. 2 is an exploded perspective view depicting parts assembled to provide a flea cage (feeding and reproduction chamber associated with an egg recovery chamber) of the embodiment depicted in FIG. 1.

FIG. 3 is an exploded vertical sectional view of the apparatus of FIG. 2.

FIG. 4 is a vertical sectional view of the apparatus of FIG. 2 in assembled form with a bed of cat and dog hair therein.

FIG. 9 is an exploded vertical sectional view of the apparatus of FIG. 8.

FIG. 10 is a vertical sectional view of the apparatus of FIG. 9 in assembled form.

FIG. 11 is an elevational view of an assembly of parts providing a plurality of flea cages (feeding and reproduction chambers each associated with an egg recovery chamber), with the individual chambers not depicted but with connector means depicted.

FIG. 12 is a horizontal sectional view taken along line 12—12 of FIG. 11 depicting the multiple feeding and reproduction chambers.

DETAILED DESCRIPTION

Figure 5:
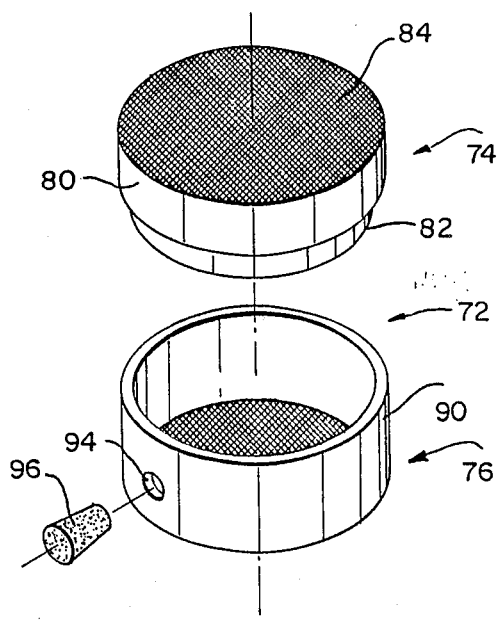
FIG. 5 is an exploded perspective view depicting parts assembled to provide a flea cage (feeding and reproduction chamber) for a second embodiment of a system herein.

Turning now to the embodiment depicted in FIGS. 1-4, said embodiment comprises a Rutledge insect blood feeder 10 associated with a membrane 12 and an assembly 14 constituting a flea cage (feeding and reproduction chamber associated with an egg recovery chamber).

The blood feeder 10 is readily available commercially from Don Lillie, Inc. of Smyrna, Georgia. The feeder 10 includes substantially bell shaped outer wall 15 surrounding a substantially frusto conical blood chamber-wall 16 and spaced therefrom to define a heat exchange fluid reservoir 18 between walls 15 and 16. Communicating with wall 15 are heat exchange fluid inlet 20 for introducing heat exchange fluid, preferably water, into reservoir 18, and heat exchange fluid outlet 22 for exit of heat exchange fluid from reservoir 18.

Stretched over the bottom of feeder 10 is membrane 12 which is preferably maintained in place by sealing to itself.

The wall 16 and the portion of membrane 12 adjacent the bottom of feeder 10 form a bloodo chamber or reservoir 24 (See FIG. 1A). The walls 15 andn 16 join at a top opening 17 which provides access into blood reservoir 24. Blood is readily introduced into reservoir 24 through opening 17 to provide a body of blood therein. The portion of membrane 12 adjacent the bottom of feeder 12 constitutes the feeding end of reservoir 24 and functions to support the body of blood in reservoir 24 which serves as the food source for fleas confined in the flea cage of the assembly 14 for mating and egg production purposes. The membrane 12 is readily penetrable by flea mouth parts for feeding and is self sealing after feeding and is preferably composed of Parafilm. In the preferred case described here the blood feeder 10 at its base and the portion of membrane 12 adjacent thereto have a diamter of about 60 mm.

The reservoir 18 is in heat exchange relation with reservoir 24. The heat exchange fluid inlet 20 is connected to a tube 26 (FIG. 1) which provides communication with a source of heat exchange fluid to supply heated fluid into reservoir 18 at a selected temperature. The heat exchange fluid outlet 22 is connected to a tube 28 which routes exiting heat exchange fluid to temperature regulating means in the form of an immersion heater-recirculator in a water tank (not depicted), e.g. a Cole-Parmer Model 1252-00 immersion heater-recirculator, for recirculation nto tube 26 at said selected temperature and passage of temperature regulated heat exchange fluid in heat exchange relation with blood in reservoir 24 whereby blood in reservoir 24 is maintained at said selected temperature.

Turning now to the flea cage 14, the parts constituting it are best depicted in the exploded views of FIGS. 2 and 3 and the assembled flea cage is depicted in FIG. 4. As depicted in FIGS. 1-4, the flea cage 14 is readily constructed utilizing three annular cross section members 30, 32 and 34. The member 30 includes an inner wall with an upper larger diameter portion 36 and a lower smaller diameter portion 38 and an outer wall with an upper larger diameter portion 42 and a lower smaller diameter portion 44 and is covered at its top end with monofilament nylon screen cloth 40 (see FIG. 2) having 300 micron interstices and is open at its bottom end. The member 32 includes an inner wall with an upper larger diameter portion 46 (the diameter is the same as that of portion 44) and a lower smaller diameter portion 48 (the diameter corresponds to that of portion 38) and an outer wall with an upper larger diameter portion 50 (the diameter corresponds to that of portion 42) and a lower smaller diameter portion 52 and is open at its top end and is covered at its bottom end with monofilament nylon screencloth 54 (see FIG. 2) having 500 micron interstices. The member 34 includes an inner wall with an upper larger diameter portion 56 (the diameter corresponds to that of portion 52) and a lower smaller diameter portion 58 (the diameter corresponds to that of portion n48) and an outer wall with an upper larger diameter portion 60 (the diameter corresponds to hat of portion 50) and a lower smaller diameter portion 62 and is open at its top end and is covered at its bottom end with monofilament nylon screencloth 64 having 30 micron interstices. The members 30, 32, 34 are sized so that they, on assembly to form cage 14, are held together by frictional engagement but are readily detached from one another for introducion of fleas, recovery of eggs and cleaning. The nylon screen cloth ends are readily joined to the acrylic rings by gluing.

The flea cage as depicted in FIG. 4 includes an upper chamber 66 which is 51 mm (about 2 inches) in diameter at its upper end (sized to interfit with the bottom of feeder 10) and has a height of 15 mm and contains a bed of cat and dog hair schematically depicted in FIG. 4 and denoted by reference numeral 68. The chamber 66 is bounded at its top end by the screencloth 40 (300 micron interstices) and at its bottom end by the screencloth 54 (500 micron interstices) and at its sides by portions 36, 38 andn 48. The cat and dog hair 68 is intertangled andn rests on screen cloth 54 and contacts screen cloth 40. The chamber 66 functions as a feeding and reproduction chamber for fleas and readily houses up to 500 fleas.

The cage 14 as indicated in FIG. 4 includes a lower chamber 70 which is bounded at its top end by the screencloth 54 (500 micron interstices) and at its bottom end by the screen cloth 64 (30 micron interstices) and at its side by portion 58. The chamber 70 functions as an egg recovery chamber.

As depicted in FIGS. 1 and 1A, the flea cage 14 is assembled with blood feeder 10 with membrane 12 thereon so that screen cloth 40 is juxtaposed to the membrane 12 at the bottom end of blood feeder 10 so that the membrane 12 bounding reservoir 24 constitutes the feeding end of reservoir 24 andn reticulated means in the form of the screencloth 40 constitutes the feeding end of chamber 66 (FIG. 4). The interstices in screen cloth 40 are sized to allow insertion of flea mout parts therethrough to penetrate through membrane 12 into blood in reservoir 24 for feeding but to prevent escape of fleas therethrough. The screen cloth 54 constitutes the egg discharge end of chamber 66 and the interstices therein are sized to allow discharge of flea eggs therethrough but to prevent escape of fleas therethrough. The interstices in screen cloth 64 are sized to preventn escape of flea eggs from chamber 70 but to allow passage of ambient air into chambers 70 and 66 to provide adequate ventilation to prevent condensation of vapor. Fibrous material in the form of bed of cat and dog hair 68 functions to provide a walking path for fleas in chamber 66 permitting them to walk to the feeding end constituted by screen cloth 40 and restricting somewhat the space in which fleas in chamber 66 are able to jump thereby providing the means influencing the approach of fleas in chamber 66 to said feeding end to conserve energy expenditure by said fleas.

Preferred practice utilizing the apparatus of FIGS. 1-4 is as follows: Cage 14, having been removed from blood feeder 10, is disassembled so that member 32 is separated from member 30. Hair bed 68 is positionend in member 32. Fleas are placed on the hair in hair bed 68, and members 30 and 32 are quickly united before the fleas can escape. Cage 14 having been reassembled with fleas therein is positioned so that screencloth 40 is under and abuts membrane 12. Host animal blood is filled into reservoir 24 through opening 17 and the temperature of the blood is maintained at 37° C. by circulation of 37° C. water through a loop constituted by the immersion heater-recirculator/water tank, tube 26, inle 20, reservoir 18, outlet 22 and tube 28 whereby the water is passed in heat exchange relation to the blood in reservoir 24 to warm theblood to 37° C. and maintain it at this temperature. The fleas confined in the breeding zone constituted by chamber 66 walk on the fibers of hair bed 68 and, are drawn by the blood in reservoir 24 to the feeding end of chamber 66 constituted by screen cloth 40 and introduce their mouth parts through the interstices of cloth 40 and penetrate membrane 12 to feed on the blood in reservoir 24. The fleas are maintained in nthe breeding zone with access to the blood in reservoir 24 foro a period fo at least 18 continuous hours. The presence of the hair bed 68 influences the approach of the fleas in chamber 66 to said feeding end to conserve energy expenditure by said fleas. Mating occurs and egg production results therefrom. The eggs fall to the bottom of chamber 66 and through the interstices of screen cloth 54 which constitutes the egg discharge end of the breeding zone. The eggs pass into chamber 70 and collect on screen cloth 64. Periodically, member 34 is detached from the assembly cnstituting cage 14, and the eggs are harvested, and adult fleas are produced therefrom by conventional methods as described hereinafter.

Figure 6:
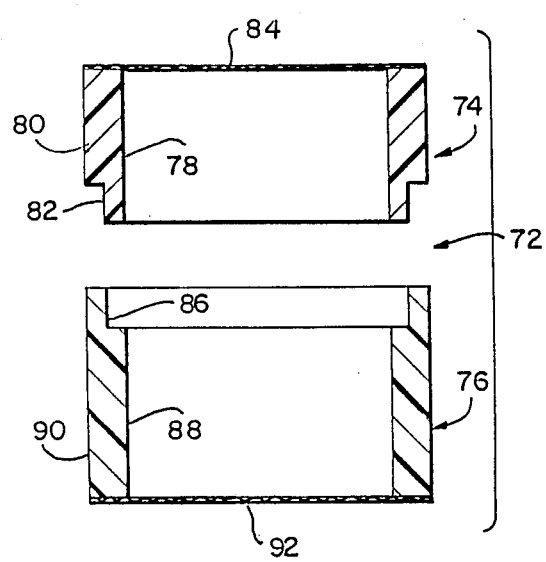
FIG. 6 is an exploded vertical sectional view of the apparatus of FIG. 5.
Figure 7:
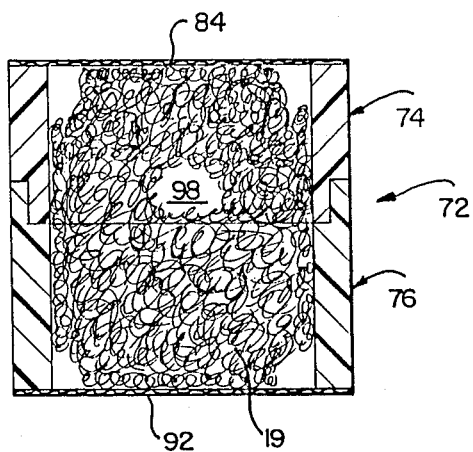
FIG. 7 is a vertical sectional view of the apparatus of FIG. 5 in assembled form with cat and dog hair positioned therein glued to the mesh top end thereof.

We turn now to the embodiment of FIGS. 5-7. These figures depict a flea cage 72 which may be substituted for cage 14 in the assembly depicted in FIG. 1.

Turning now to the assembly constituting a cage 72, the parts constitutign it are best depicted in the exploded views of FIGS. 5 and 6 and the assembled cage is depicted in FIG. 7. As depicted in FIGS. 5-7, the cage 72 is readily constructed of two annular cross section members 74 and 76. The member 74 includes an inner wall 78 and an outer wall with an upper larger diameter portion 80 and a lower smaller diameter portion 82 (see FIG. 6) and is covered at its top end with monofilament nylon screen cloth 84 (see FIG. 5) having 300 micron interstices and is open at its bottom end. The member 76 (FIG. 6) includes an inner wall with an upper larger diameter portion 86 (the diameter corresponds to that of portion 82) and a lower smaller diameter portion 88 (the diameter corresponds to that of wall 78) and an outer wall 90 (the diameter corresponds to that of portion 80) and is open at its top end (FIG. 5) and is covered at its bottom end with monofilament nylon screencloth 92 (FIG. 6) having 500 micron interstices. The member 76 (FIG. 5) contains an opening 94 (e.g. 10 mm in diameter) in its sidewall providing access from the outside into the interior of cage 72. The opening 94 receives a cork plug 96. The members 74 and 76 except for the nylon screen cloth portions are constructed of transparent acrylic plastic. The members 74 and 76 are sized so that they, on assembly to form cage 72, are held together by frictional engagement but are readily detached from one another.

The assembly 72 as depicted in FIG. 7 includes a single chamber 98 which is 51 mm (about 2 inches) in diameter (sized to interfit with the bottom of blood feeder 10) and has a height of 37 mm and contains abed of intertangled dog and cat hair which is denoted by reference numeral 19. The bed of hair 19 rests on screen cloth 92 and extends to screen cloth 84 where it is glued at two 5 mm diameter spots. The top end of chamber 98 is constituted by the screen cloth 84 (300 micron interstices) and its bottom end by screen cloth 92 (500 micron interstices) and the side of chamber 98 is formed by portions 78 andn 88. The chamber 98 functions as a feeding and reproduction chamber for fleas and readily houses up to 500 fleas.

The flea cage 72 is assembled with blood feeder 10 with membrane 12 thereon by substituting cage 72 for cage 14 in the apparatus of FIGS. 1 and 1A so hat screen cloth 84 is juxtaposed to membrane 12 at the bottom end of blood feeder 10 so hat the membrane 12 bounding reservoir 24 constitutes the ffedign end of reservoir 24 and reticulated means in the form of the of screen cloth 84 constitutes the feeding end of chamber 98. The screen cloth 92 constitutes the egg discharge end of the chamber 98. Fibrous material in the form of the hair 19 functions to provide a walking path for fleas in chamber 98 permitting them to walk to the feeding end of chamber 98 thereby providing means influencing the approach of fleas in chamber 98 to said feeding end to conserve energy expenditure by said fleas.

Preferred practice with apparatus utilizing blood feeder 10 and membrane 12 as depicted in FIGS. 1 and 1A with flea cage 72 of FIGS. 5–7 substituted for the flea cage 14, is the same as the preferred practice described in conjunction with FIGS. 1–4 except for differences in methods of insertion of the fleas into the feeding and reproduction chamber, the way of influencing the approach of the fleas to the feeding end to conserve energy expenditure by the fleas, and the method of egg recovery. In the embodiment based on flea cage 72, the fleas are inserted periodically into the breeding and reproduction chamber (chamber 98) defining the breeding zone by removing cork plug 96 and placing fleas by means of a funnel into the breeding zone via access opening 94 whereupon cork 96 is replaced to confine the fleas in chamber 98. Influencing of the approach of the fleas to the feeding end of chamber 98 is carried ou by providing walking paths in the form of cat and dog hairs 19. So far as egge recovery is concerned, no egg recovery chamber is provided. Eggs exit via the interstices in screen cloth 92 and are recovered thereunder, for example, on a paper towel.

Figure 8:
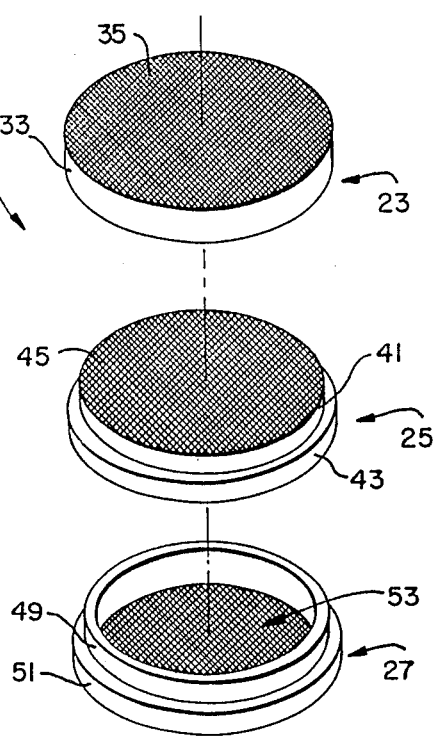
FIG. 8 is an exploded perspective view depicting parts assembled to provide a flea cage (feeding and reproduction chamber associated with an egg recovery chamber) for a third embodiment of a system herein.

We turn now to the embodiment of FIGS. 8–10. These figures depict a flea cage 21 which may be substituted for cage 14 in the assembly depicted in FIG. 1.

Turning now to the assembly constituting the cage 21, the parts constituting it are best depicted in the exploded views of FIGS. 8 and 9 and the assembled cage is depicted in FIG. 10. As depicted in FIGS. 8–10, the cage 21 is readily constructed of three annular cross section members respectively denoted by reference numerals 23, 25 and 27. The member 23 (FIG. 9) includes an inner wall with an upper smaller diameter portion 29 and a lower larger diameter portion 31 and an outer wall 33 and is covered at its top end with monofilament nylon screen cloth 35 (see FIG. 8) having 300 micron interstices and is open at its bottom end. The member 25 (FIG. 9) includes an inner wall with an upper smaller diameter portion 37 (the diameter corresponds to that of portion 29) and a lower larger diameter portion 39 and an outer wall with an upper smaller diameter portion 41 (the diameter corresponds to that of portion 31) and a lower larger diameter portion 43 (the diameter corresponds to that of wall 33) and is covered at its top end with monofilament nylon screen cloth 45 (see FIG. 8) having 500 micro interstices and is open at the bottom. The member 27 (FIG. 9) includes an inner wall 47 (having a diameter corresponding to the diameter of portion 37) and an outer wall having an upper smaller diameter portion 49 (having a diameter corresponding to the diameter of portion 39) and a lower larger diameter portion 51 (having a diameter corresponding to that of portion 43) and is open at the top and is covered at its bottom with monofilament nylon screen cloth member 53 (see FIG. 8) havign 30 micron interstices. The membrs 23, 25, and 27 except for the nylon screen cloth portions are constructed of transparent acrylic plastic. The members 23, 255 and 27 are sized so that they, on asesmbly to form cage 21, are held together by frictional engagement but are readily detached from one another.

The assembly constituting cage 21 as depicted in FIG. 10 includes an upper chamber 55 and a lower chamber 57.

The chamber 55 is bounded at its top end by screen cloth 35 (300 micron interstices) and at its bottom end by screen cloth 45 (500 micron interstices) and at its side by portion 29. Chamber 55 is 51 mm (about 2 inches) in diameter (sized to interfit with the bottom of feeder 10 of FIG. 1) and has a height of 1.6 mm. The chamber 55 functions as a feeding and reproduction chamber for fleas and readily houses up to 100 fleas.

The chamber 57 is bounded at its top by screen cloth 45 (500 micron interstices) and at its bottom by screen cloth 53 (30 micron interstices) and at its side by portions 37 and 47. The chamber 57 has a diameter of 51 mm (about 2 inches) to correspond with that of chamber 55 and a height of about 15 mm. The chamber 57 functions as an egg recovery chamber.

The flea cage 21 is assembled with blood feeder 10 with membrane 12 thereon by substituting cage 21 for cage 14 in the apparatus of FIGS. 1 and 1A so that screen cloth 35 is juxtaposed to membrane 12 at the bottom end of blood feeder 10 so that the membrane 12 bounding reservoir 24 constitutes the feeding end of reservoir 24 and reticulated means in the form of the screen cloth 35 constitutes the feeding end of chamber 55. The screen cloth 45 constitutes the egg discharge end of the chamber 55. The small height dimension of chamber 55 restricts jumping by fleas in chamber 55 thereby providing means influencing the approach of fleas in chamber 55 to he feeding end thereof to conserve energy expenditure by said fleas. This use of a narrow height dimension in the breeding and reproduction chamber is advantageous compared to providing fibrous walkways in such chamber as a means for influencing the approach of fleas in such chamber to said feeding end to conserve energy expenditure of such fleas when the flea cages are constructed of transparent material because a clear view of the fleas in the chamber is afforded whereas providing fibrous pathways (including animal hair) as in the embodiments of FIG. 4 and 7 obstructs viewing.

Preferred practice with apparatus utilizing blood feeder 10 and member 12 as depicted in FIGS. 1 and 1A with flea cage 21 of FIGS. 8–10 substituted for the flea cage 14, is the same as the preferred practice described in conjunction with FIGS. 1–4 except for the method of insertinng the fleas and except for the method of influencing the approoch of the fleas to the feeding end to conserve energy expenditure by the fleas. The fleas are inserted by separating member 23 from member 25, cooling the fleas to a state of inactivity, positioning member 23 so that screen cloth 35 is at the bottom, placing the dormant fleas on screen cloth 35 in inverted member 23, reuniting members 23 and 25, and then reinverting the assembly so that screen cloth 35 is at the top. Influencing of the approach of the fleas to the feeding end of the breeding zone so as to conserve energy expenditure on the part of the fleas is carried out only by resticting jumping by fleas in said breeding zone by utilizing a breeding zone of small height dimension rather than by providing fibrous pathways to permit the fleas to walk rather than jump.

We turn now to the embodiment of FIGS. 11 and 12. These figures depict a flea cage 59 which may be substituted for cage 14 in the assembly depicted in FIGS. 1 and 1A.

Turning now to the assembly constituting flea cage 59, it is made up of three plates with bores therethrough and associated screen cloth members. As depicted in FIG. 11, cage 59 includes a bottom plate 61, having screen cloth member 63 (having 30 micron interstices) attached at its underside. The plate 61 abuts and is removably attached along parting plane 65 to a middle plate 67 which has its top covered with screen cloth member 69 (having 5000 micron interstices). Member 69 abuts a top plate 71 which has its top covered with a screencloth member 73 (having 300 micron interstices). The members 73, 71, 69 and 67 are attached together using a single centrally located screw 75. The plates 61, 67 and 71 each containg eight corresponding axially extending bores to define together with said screencloth members eight feeding and reproduction chambers each associated with its own egg recovery chamber. FIG. 12 which depicts a horizontal section through plate 71 shows the eight feeding and reproduction chambers 77a, 77b, 77c, 77d, 77e, 77f, 77g, 77h. The height dimension of each feeding and reproduction chamber is 1.6 mm and the height dimension of each egge recovery chamber is 15 mm. Each feeding and reproduction chamber readily houses up to 10 fleas. The diameter of theentire cage 59 is 51 mm (abou 2 inches). Thus, in this embodiment, a single blood feeder and associated membrane serves a plurality of feeding and reproduction chambers. This apparatus is useful for practice involving a plurality of smallg roups of fleas.

In the preferred use of the flea cage 59, the screw 75 is removed to allow removal of plate 71 and fleas cooled to inactivity are positioned for confinement in selected chambers. The flea cage is then reassembled and positioned instead of cage 14 in the apparatus of FIGS. 1 and 1A with member 73 in juxtaposition to membrane 12 associated blood feeder 10.

The method used in conjunction with cage 59 as part of othe apparatus is similar to the method where cage 21 of FIGS. 8–10 is used part of the appratus in that the fleas in a feeding and reproduction chamber are provided access to he tempeature regulated blood for a period of at least 18 continuous hours and the 1.6 mm height dimension in the breeding zone of each feeding and reproduction chamber restricts jumping by the fleas in a breeding zone to conserve expenditure of energy by said fleas.

Other information about apparatus herein includes the following:

While the above described blood feeer 10 is the only one known to the inventors to be commercially available, other blood feeders may be used so long as they contain a blood reservoir wall structure adapted to join with meansn penetrable by blea mouth parts for feeding and a means for regulating blood ins aid reservoir to a selected temperature.

The area of the membrane under the body of blood in a blood feeder used herein preferably is such that the membrane will have sufficient strength to support said body of blood when the blood feeder is lifted off the cage thereunder for membrane replacement. Thus, for a circular cross section blood feeder, the diameter preferably should not exceed approximately 60 mm when parafilm is used said membrane. However, larger diameter structures are readily used, if, for example, a blood is removed from above the membrane before the blood feeder is lifted off the cage thereunder or if structure is provided to support or reinforce the membrane.

The membrane 12 should have a thickness at the location of feeding which is penetrable by the fleas for feeding on blood thereabove, normally from 0.001 to 0.005 inches. Parafilm as described above is a preferred material of construction foro the membrane as it has been found to be useful for feeding without leakage occurring over a suitable feeding period. Parafilm is described in the Concise Chemical and Technical Dictionary (1974 edition) edited by H. Bennett as paraffin wax modified with an elastomer to give a flexible, thermoplastic sheet or filmand by a representative of the manufacturer as composed of a blend of wax, elastomer and polyolefin. Other membranes besides parafilm membranes indicated in literature to be useful for blood feeders are natural membranes including membranes made of mouse, rat, rabbit, flying squirrel or chicken skin, cattle cecum ("Silverlight" or Baudruche), sausage casing, condom material (sheep casing), and artificial membranes of Cellophane, Saran Wrap, agar, gold beater, and gutta percha.

The mesh sizes for screencloth at the feeding end of a feeding and reproduction chamber of a flea cage should be large enough to allow access by flea mout parts to blood in the adjacent reservoir but small enough to prevent escape of the fleas through the mesh. Mesh with interstices of 250 to 400 microns provide these characteristics.

The mesh sizes for screen cloth at the egg discharge end of a feeding and reproduction chamber of a flea cage should be large enough to allow discharge of eggs but small enough to prevent escape of fleas through the mesh. Mesh with interstices of 400 to 600 microns provide these characteristics.

The mesh sizes for screen cloth at the egg collection end of an egg recovery chamber of a flea cage should be small enough to retain eggs discharged to said chamber but large enough to allow circulation of air to prevent condensation. Mesh with interstices of 15 to 30 microns is suitable for this purpose.

The screen cloth is preferably one that is commercially available and can be of metal or plastic, and preferably is of nylon (Nitex Screening Fabric). Aluminum mesh is also suitable.

The wall structure of the flea cages is preferably of transparent material to allow viewing but can be of opaque material. Acrylic plastic is a preferred material of construction. Other suitable materials of construction include, for example, polyvinyl chloride, polyethylene, polypropylenle and Teflon.

In above-described embodiments the flea cages are made from parts machined to fit together with friction joints. However, other assembly/disassembly means can be provided, such as threads or pins.

The fibrous material for use in flea cages to provide walking paths foro the fleas in pursuit of access to feeding should have a diameter accommodating gripping by the claws of the fleas being bred. Cat and dog hair having diameters ranging from 8 to 140 microns are preferred materials especially for fleas where the normal animal host is a cat or dog. Other furs or hair are also suitable especially such that is available inexpensively in quantity. Artifical fibers are also useful so long as they do not cut the fleas. For example polyester or nylon fibers are suitable.

As indicated above, the means influencing the approach of the fleas to the feeding end of a feeding and reproductionn chamber to conserve energy expenditure by the fleas can be either the provision of othe interior of said chamber with a height dimension so as to restrict jumping by the fleas or the inclusion in said chamber of fibrous means permitting the fleas to walk to the feeding end of the chamber.

The approach of providing the interior of the chamber with a height dimension so as to restrict jumping involves use of a height dimension ranging from 1.4 to 1.8 mm. Height dimensions less than 1.4 mm have the disadvantage of restricting the mobility of the fleas to the extent that mating is hindered. Height dimensions more than 1.8 mm allow sufficient jumping room so hat sufficient energy may be expended by fleas in pursuit of feeding so that feeding and mating. is inhibited. For feeding and reproduction chambers with a height dimension of 1.4–1.8 mm, the height dimension itself fosters conservation of energy expenditure on the part of the fleas therein and the inclusion of fibrous material in the chamber is not necessary.

For feeding and reproduction chambers with height dimensions exceeding 1.8 mm up to about 20 mm, fibrous material providing walkways for the fleas to the feeding area can be in the form of a ball or mat or bed of intertangled fibers simply laid in the chamber allowing walking approach preferably to within 1.8 mm of the feeding area.

For feeding and reproduction chambers with a height dimension from about 20 mm to about 60 mm or greater, the fibrous material providing the walkways for the fleas is preferably glued to portions of the chamber boundaries. The important point is that the fibrous material should be positioed to provide walking approach to the feeding end of the chamber.

Other information about the process herein is as follows:

The process herein is considered to be applicable to all species of fleas. It is especially useful in regard to fleas of economic importance to dogs, cats and humans, namely *Ctenocephalides felis, Ctenocephalides canis, Xenopsylla cheopis,* and *Pulex irritans.*

The hosts reported for *Ctenocephalides felis* include dog, cat, man, cattle, buffalo, sheep, goat, raccoon, gray fox, red fox, coyote, bobcat, jackal, opossum, short-tailed shrew, rabbit, rat, red squirrel, hedgehog, greater yellow bat, mongoose, and common myna.

The hosts reported for *Ctenocephalides canis* includes dog, cat, man, gray fox, coyote, ground squirrel, rat, striped skunk, buffalo, sheep, goat and opossum.

The hosts reported for *Xenopsylla cheopis* include rodents, such as the rat and mouse, man, sheep, goat, shrew, and mongoose.

The hosts reported for *Pulex irritans* include man, ppig, prairie dog, rat, badger, rabbit, sheep, goat, cattle, deer, dog, cat, skunk, coyote, gray fox, bobcat, desert kit fox, weasel, opossum, chicken, burowing owl and cuckoo.

The blood for use as feed should be the blood of a host animal. Foro *C. felis,* the preferred blood is dog blood or cattle blood which have been found to be equally effective. While at blood is useful for *C. felis,* it is difficult to obtain in sufficient quantity even for moderate usage and is expensive.

The blood is preferably used in conjunction with an anticoagulant such as 20% sodium citrate used, for example, in an amount of 35 ml of 20% sodium citrate per liter. The blood is readily stored under refrigeration, e.g. at 4° C., for up to two weeks prior to use and is storable for even a longer period if drawn under sterile conditions.

The temperature of the blood in the process herein preferably maintained in the range of 35° C. to 39° C. and most preferably is 37° C..

Twenty four hours appears to be the practical limit for replacement of the blood in the process herein because if the blood is left longer, it clots and bacterial contamination increases. Moreover, with the apparatus described in the preferred embodiments herein, the blood has to be replaced on or before 24 hours of use as by 24 hours the feeding membrane requires replacement because it becomes too leaky due to weakening because of feeding penetrations by flea mouth parts and with such apparatus replacement of the feeding membrane requires replacement of the blood in the blood reservoir.

Where the fleas are immobilized to dormant state for transfer into apparatus for carrying out a process herein, this is readily carried by refrigerating them by exposure to 4° C. for thirty minutes.

The male to female ratio of the fleas inserted into the flea cages for the process herein preferably ranges from 1:10 to 1:1.

As indicated hereinbefore, it is important to satisfactory breeding results that the fleas should be provided continuous access to the host animal blood food source for at least 18 hours and a preferred continuous access period ranges from 22 to 24 hours. About twenty four hours of continuous access is the practical limit with the apparatus disclosed as the blood feeding membrane must be replaced by this time.

The life span of the fleas determines the maximum period for maintaining then in a cage. For most fleas, this period is about a month.

Preferably, eggs are harvested each day.

As indicated hereinbefore, production of fleas from eggs is readily carried out by conventional methods. In a preferred method, collected eggs are placed on autoclaved sand in a 100×25 mm plastic petri dish in an incubator at 27° C. and 80–85% relative humidity. After two days, the eggs hatch into larvae and are maintained ithe incubator and supplied with ground dried cattle blood for food (the dried blood is added every other day). After 7–10 days the cultures are sieved to recover pupae. The pupae are placed in tissue culture flasks with the caps modified to include nylon mesh with 300 micron interstices for admission of moist incubator air. The pupae in said modified flasks are maintained in the incubator at 27° C. and 80–85% relative humiditty whereupon the pupae develop into adult fleas. With the above procedure the eggs are converted into adult fleas within 14 days.

The following specific example is illustrative of the invention:

EXAMPLE

Eggs obtained from c. felis on cats and dogs in Ithaca, New York were used to start laboratory colonies.

Eggs so obtained or produced by further generations were matured into adult fleas by the preferred procedure described above.

Adult fleas emerging from the pupal stage were transferred into cages as described in conjunction with FIGS. 2–4, into cages as described in conjunction with FIGS. 5–7 into cages as described in conjunction with FIGS. 8–10 and into cages as described in conjunction with FIG. 11 and 12. The cages were each used in conjunction with a blood feeder 10 and a parafilm membrane 12 (formed from flm of 0.005 inch initial thickness stretched in two directions). The feeders were each filled with 10 ml. of blood daily and the membranes were changed daily. The blood was either cattle blood collected in a liter bottle to which 35 ml of 20% sodium citrate was added or dog blood collected in 15 ml EDTA coated vacutainer tubes. The blood was collected weekly and stored in a refrigerator at 4° C. for use within a week. The blood in the feeders wasmaintained at 37° C.. The fleas were provided with access to the blood in a feeder for 24 continuous hours. In the case of the cages of FIGS. 2-4 and 5-7, the fleas were influenced to conserve energy expenditure in feeding by the provision of dog and cat hair pathways serving as a scaffolding for walking to the feeding membrane. In the case of the cages of FIGS. 8-10 and 11-12, the fleas were forced to expend minimum energy in feeding because the 1.6 mm height dimension restricted jumping by the fleas. Eggs wer harvested daily and matured into adult fleas by the preferred procedure set forth above. The result in the cae of each of the cages was a reproduction output of 13-19% of that of *C. felis* fed on cats. The apparatus and method functioned to practically breed fleas. The results for use of dog blood were essentially the same as for the use of cattle blood.

Other variations will be evident to those skilled in the art. Therefore, the scope of the invention is intended to be defined by the claims.

What is claimed is:

1. System for breeding fleas without having them feed on host animals, said system comprising
   (a) containing means for functioning in combination with means penetrable by flea mouth parts for feeding to provide a blood reservoir means,
   (b) means for maintaining blood placed in said reervoir means at a selected temperature level,
   (c) feeding and reproduction chamber means for housing fleas for breeding, said chamber means being such as to prevent escape of fleas therefrom and having (i) an interior, (ii) an end for juxtaposition to said penetrable means and (iii) an egg discharge end for discharge of eggs therethrough,
   (d) means influencing approach by said fleas to said end (c)(ii) to conserve energy expenditure by said fleas to the extent of obtaining a reproduction output at least 10% of the reproduction output of fleas feeding on host animals, said means (d) being selected from the group consisting of (i) providing said interior (c)(i) with a height dimension such as to restrict jumping by fleas housed therein and (ii) fibrous means in said interior (c)(i) providing a path permitting fleas to walk thereon substantially to said end (c)(ii) thereby influencing fleas to walk on said path instead of jumping.

2. System as recited in claim 1, wherein said penetrable means comprises a substantially self-sealing film membrane.

3. System as recited in claim 2, wherein said film is flexible film of composition comprising elastomer and wax.

4. System as recited in claim 3, wherein said film is flexible film composed of a blend of wax, elastomer and polyolefin.

5. System as recited in claim 1, wherein said element (b) comprises heat exchange means comprising means for circulating heated fluid in heat exchange relation with blood placed in said reservoir means.

6. System as recited in claim 1, wherein said means (d) comprises fibrous means in said interior (c)(i) permitting fleas to walk thereon substantially to said end (c)(ii).

7. System as recited in claim 6, wherein said fibrous means comprises animal hair selected from the group consisting of dog hair and cat hair.

8. System as recited in claim 1, wherein said means (d) comprises providing said interior (c)(i) with a height dimension so as to restrict jumping by fleas housed therein.

9. System as recited in claim 8, wherein said height dimension ranges from 1.4 to 1.8 mm.

10. System as recited in claim 1, wherein said egg discharge end of said chamber means (c) comprises reticulated means having interstices sized to allow passage of eggs therethrough but to prevent escape of fleas from said chamber means (c), said egg discharge end communicating with an egg recovery chamber.

11. Method for breeding fleas without having the fleas feed on a host animal, said method comprising the steps of
    (a) confining fleas in a breeding zone having a feeding end and an egg discharge end,
    (b) proving an inanimate flea-accessible source of host animal blood at a selected temperature at said feeding end,
    (c) maintaining the fleas in said breeding zone with access to said blood for a period of at least 18 continuous hours
    (d) influencing approach by said fleas to said feeding end to conserve expenditure of energy by said fleas, thereby to foster feeding, mating and egg production,
    (e) discharging eggs from said breeding zone and recovering said eggs for production of adult fleas therefrom.

12. Method as recited in claim 11, wherein the fleas confined in said breeding zone are of species Ctenocephalides felis and the blood utilized is dog blood or cattle blood.

13. Method as recited in claim 12, wherein said blood is maintained at a temperature ranging from 35° C. to 39° C..

14. Method as recited in claim 13, wherein said blood is maintained at a temperature of 37° C.

15. Method as recited in claim 11 wherein said continuous access period ranges about 22 to about 24 hours.

16. Method as recited in claim 15 wherein said influencing of approach bys aid fleas to said feeding end comprises restricting jumping by the fleas in said breeding zone.

17. Method as recited in claim 15 wherein said influencing of approach by said fleas to said feeding end comprises providing a walking path substantially to said feeding end thereby influencing fleas to walk on said path instead of jumping.

18. Method as recited in claim 11 wherein the conserving of energy in step (d) is such as to obtain a reproduction output at least 10% of the reproduction output of fleas feeding on host animals.

19. Method as recited in claim 18 wherein step (d) is selected from the group consisting of (i) restricting jumping by the fleas in the breeding zone or (ii) providing a walking path for the fleas to said feeding end.

* * * * *